United States Patent [19]

Landreneau

[11] Patent Number: 4,681,564
[45] Date of Patent: Jul. 21, 1987

[54] CATHETER ASSEMBLY HAVING BALLOON EXTENDED FLOW PATH

[76] Inventor: Michael D. Landreneau, Mai Kai Apt. #29, 300 Samfor Ave., Shreveport, La. 71103

[21] Appl. No.: 789,821

[22] Filed: Oct. 21, 1985

[51] Int. Cl.⁴ .................... A61M 29/02; A61M 31/00
[52] U.S. Cl. ........................................ 604/97; 604/96; 604/29; 604/280
[58] Field of Search ...................... 604/29, 43, 96, 97, 604/280, 282

[56] References Cited

U.S. PATENT DOCUMENTS

| | | |
|---|---|---|
| 3,144,868 | 8/1964 | Jascalevich . |
| 3,221,151 | 10/1965 | Foderick et al. . |
| 3,394,705 | 7/1968 | Abramson . |
| 3,438,375 | 4/1969 | Ericson . |
| 3,459,175 | 8/1969 | Miller . |
| 3,640,269 | 2/1972 | Delgado ............................ 604/280 |
| 3,823,720 | 7/1974 | Tribble . |
| 3,888,249 | 6/1975 | Spencer ............................ 604/280 |
| 3,902,492 | 9/1975 | Greenhalgh . |
| 4,184,497 | 1/1980 | Kolff et al. ....................... 604/27 |
| 4,351,342 | 9/1982 | Wiita et al. ...................... 604/43 |
| 4,392,855 | 7/1983 | Oreopulos et al. ............... 604/280 |
| 4,437,856 | 3/1984 | Valli ................................ 604/29 |
| 4,445,897 | 5/1984 | Ekbadh et al. ................... 604/280 |
| 4,552,557 | 11/1985 | Rangaswamy ................... 604/96 |

Primary Examiner—Stephen C. Pellegrino
Assistant Examiner—John D. Ferros
Attorney, Agent, or Firm—Cushman, Darby & Cushman

[57] ABSTRACT

A catheter assembly for insertion through a surgical opening into an interior body space for enabling a fluid to be introduced into said body space and for enabling unwanted flowable material to be drained from the body space including fluid after the same has been introduced therein. The catheter assembly comprises three separate fluid passages extending within exterior and interior end sections thereof. A balloon structure is in communication with a first passage. A second passage has outlet openings communicating therewith through which treating fluid is introduced into the body space. A third passage has drain openings communicating therewith through which fluid and/or unwanted flowable material in the body space can pass therefrom. The first passage has one or more inflation openings communicating therewith through which inflating fluid is received for passage into the balloon structure to inflate the same so as to cause fluid passing into the body space through the outlet openings to follow a more extensive flow path within the body space in order to reach the drain openings and the drain openings to be maintained substantially operationally free of obstruction by tissue defining the body space than is the case when the balloon structure is deflated within the body space immediately following insertion therein or just prior to withdrawal therefrom.

7 Claims, 13 Drawing Figures

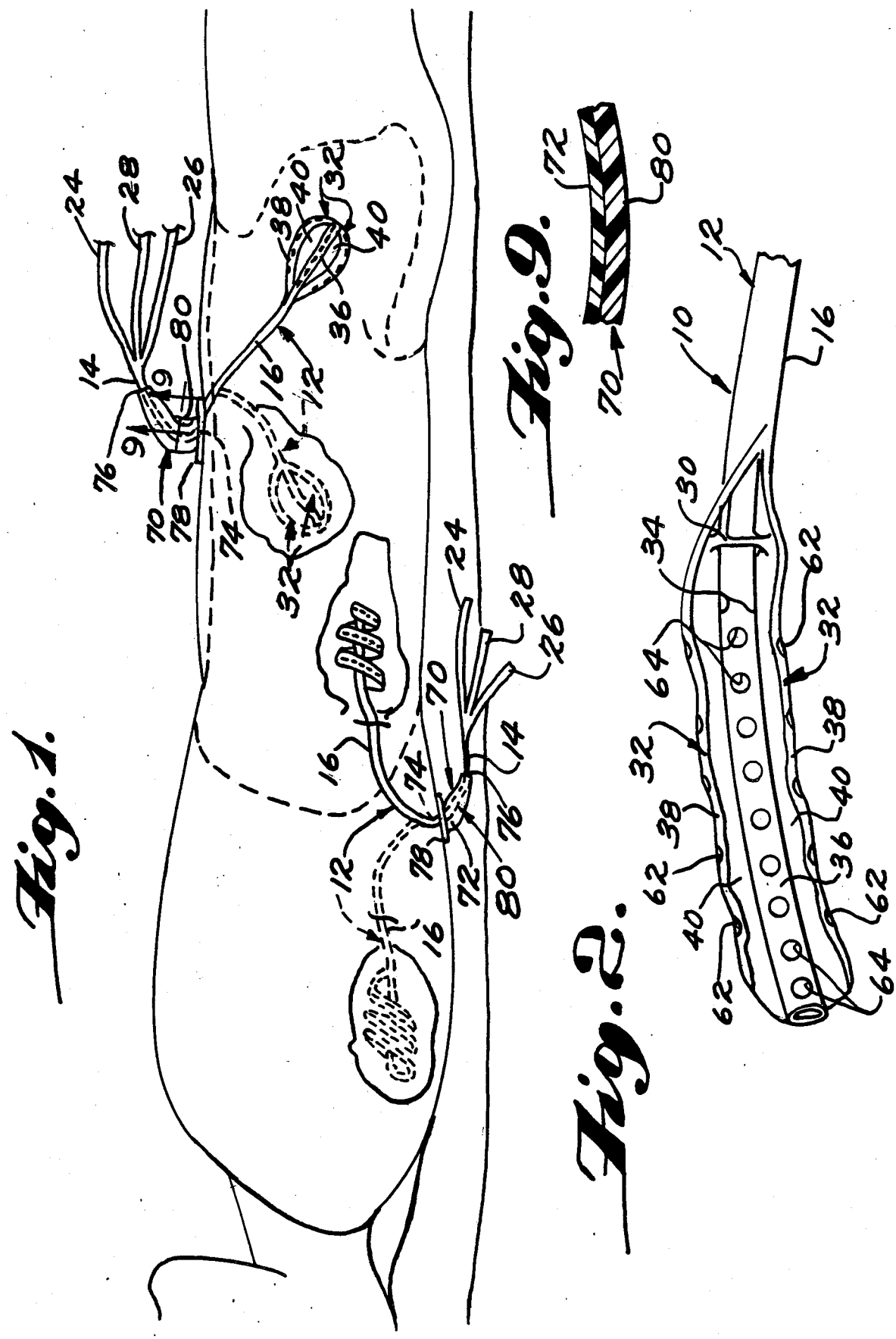

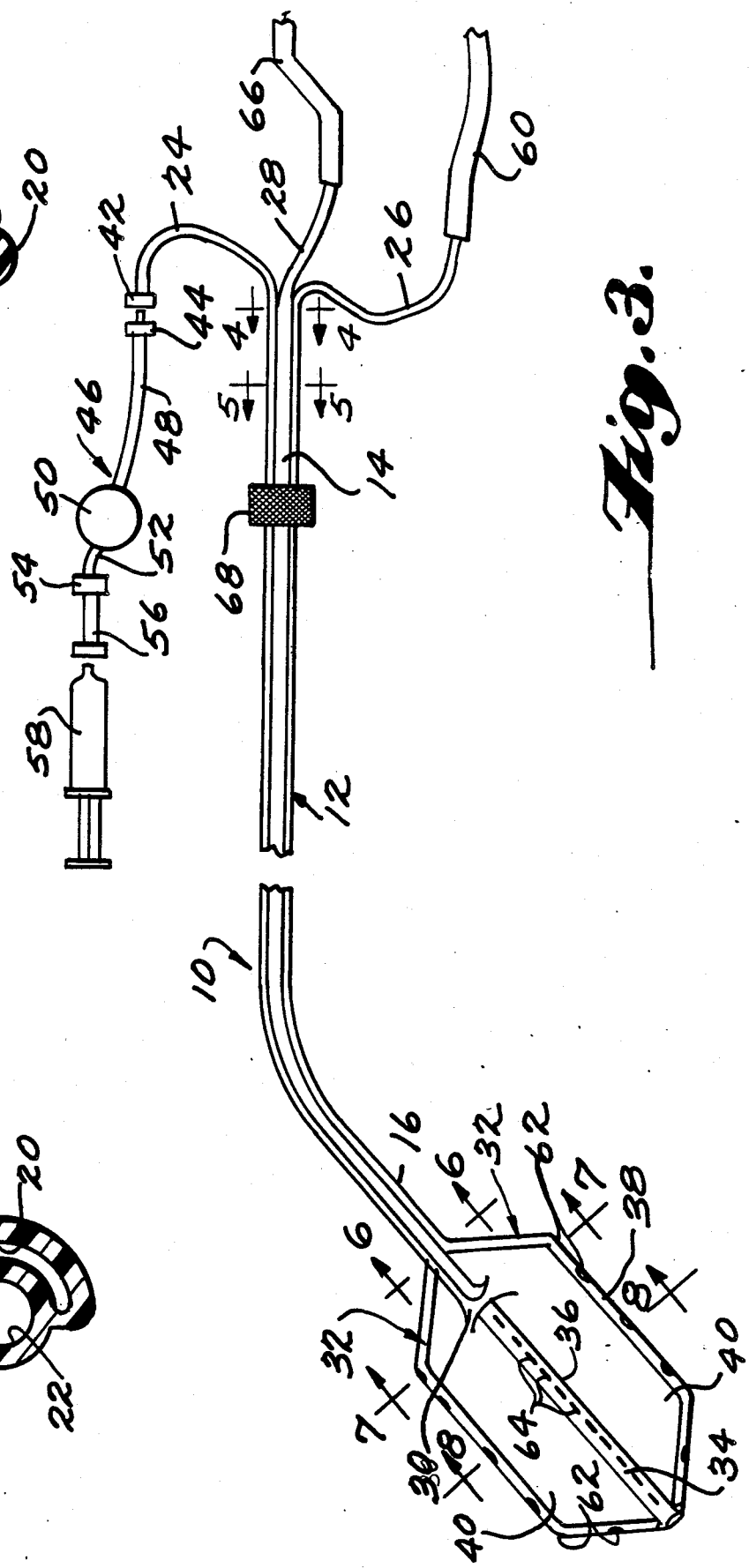

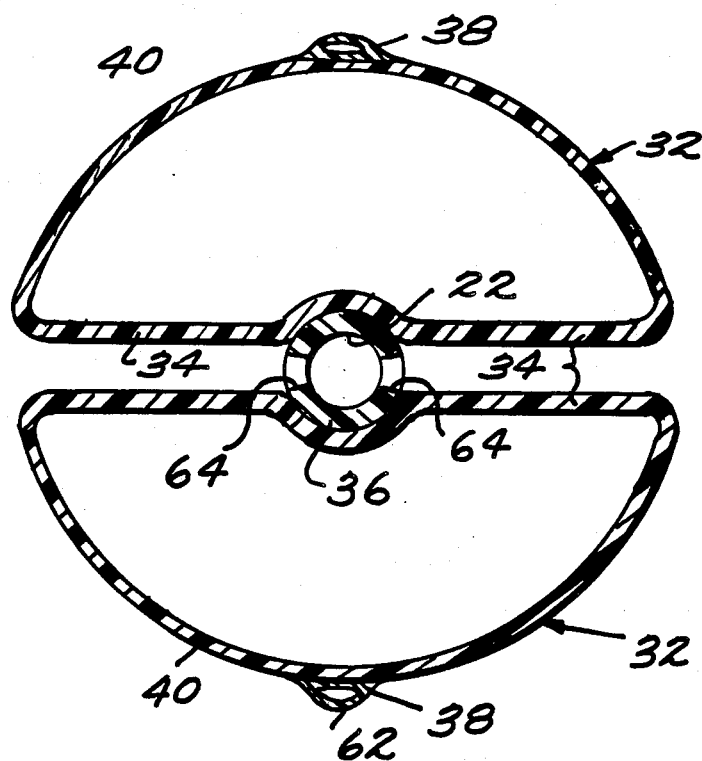
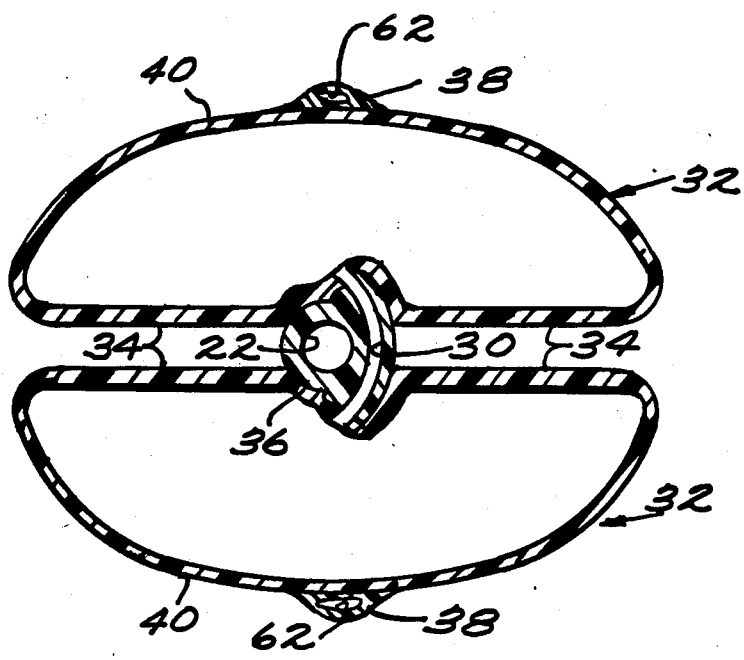

CATHETER ASSEMBLY HAVING BALLOON EXTENDED FLOW PATH

This invention relates to medical catheters and more particularly to an improved catheter assembly for insertion through a surgical opening into an interior body space for enabling a fluid to be introduced into the body space and for enabling unwanted flowable material to be drained from the body space including fluid after the same has been introduced therein.

The catheter assembly of the present invention is distinguished from catheters of the type which are adapted to be inserted through naturally existing body passages into an interior body space, such as a body cavity communicating with the passage. The present catheter assembly is basically distinguished in that it is adapted to be inserted through a surgical opening into the body space as distinguished from a natural passage. Surgical procedures where the present catheter assembly would be useful include peritonoeal dialysis and the irrigation and drainage of abscesses in body spaces including natural body cavities in the following situations: pelvic abscess; perienteric abscess, pancreatitis; pericolonic abscess; perihepatic abscess; perinephric abscess; paragastro-duodenal abscess; retroperitoneal abscess; pancreatic abscess; empyema.

Examples of patents disclosing devices for use in irrigating and draining body spaces to which surgical access must be obtained include U.S. Pat. Nos. 3,144,868 and 3,823,720. In both of these patents the assembly includes the utilization of essentially two separate individual catheters, one of which is used as a drainage tube for withdrawing fluids and unwanted flowable material from the body space and the other of which is utilized as an irrigation tube for feeding irrigation fluid into the body space. In the device disclosed in the earlier of these two patents the catheter assembly also includes a conventional retention balloon structure. The balloon operates in more-or-less conventional fashion to provide for the retention of the catheter within the body space and to provide a more effective seal between the exterior of the catheter tube passing through the surgical opening and the interior of the surgical opening.

Retention and sealing balloons are conventionally embodied in so-called Foley catheters an example of which is disclosed in U.S. Pat. No. 3,211,151. A later U.S. Pat. No. 3,438,375 discloses a retention balloon of somewhat more elaborate construction which, in addition to the retention function, also serves to preclude body tissue from being drawn into the drainage openings during and after the draining period. The typical Foley catheter and variation thereof exemplified in the two patents identified above do not provide for the introduction of fluid into the body cavity being drained.

It has been proposed in the patent literature to provide for both irrigation and drainage in a catheter assembly in situations where conventional Foley catheters are utilized as for example in the bladder.

Examples of retention and sealing balloons in catheter assemblies which are adapted to irrigate and drain cavities such as the bladder, the colon, etc., through which access can be obtained by natural passages are disclosed in U.S. Pat. Nos. 3,394,705, 3,459,175, and 3,902,492. A similar construction is embodied in the so-called "Murphy Drip Catheter" produced by L. P. Bard, Inc.

Most of the several uses herein contemplated for the catheter assembly of the present invention involve the need to drain puss and other deleterious material associated with abscess and the need to augment such drainage by irrigation. The nature of the unwanted material which must be drained or made to flow through the drain openings of the catheter assembly, as well as the need to accommodate the return circulation of the irrigation fluid, makes it quite important to keep the drain openings functioning at full capacity and free from body tissue obstructions which would materially diminish the effectiveness of the procedure being carried out. Moreover, the effectiveness of the procedure in most instances is dependent upon the effectiveness of the irrigation fluid circulation established and the ability of the same to loosen the unwanted material throughout the body space and assist in moving it to the drain openings for passage therethrough.

The effectiveness of the irrigation fluid circulation is of significance in peritoneal dialysis even though the circulating fluid in peritoneal dialysis which reaches the drain openings does not contain particles tending to cause blockage to the same extent as fluid containing puss and other deleterious material associated with abscess. In peritoneal dialysis it is basically important to circulate the dialysis fluid in contact with the body tissue. It is important to maintain the drain openings free from blockage by the body tissue so that circulation will continue.

It is an object of the present invention to provide a catheter assembly suitable for use in the medical procedures heretofore stated which is operable to provide the enhanced effectiveness previously described. In accordance with the principles of the present invention, this objective is achieved by interrelating the irrigation outlet openings and draining openings in the interior end section of the catheter tubular structure with a balloon structure carried thereby in such a way that the inflation of the balloon structure after insertion within the body space has the effect of causing fluid passing through the outlet openings into the body space to follow a more extensive flow path within the body space in order to reach the drain openings and the drain openings to be maintained substantially operationally free of obstruction by tissue defining the body space than is the case when the balloon structure is deflated within the body space immediately following insertion therein or just prior to withdrawal therefrom.

Preferably, the interior end section of the tubular structure of the catheter assembly defining the irrigation passage is carried by the portions of the balloon structure which extend the most peripherally usually into contact with the body space walls and the outlet openings are formed therein so that fluid passing therethrough enters the body space along the walls thereof and is directed by the periphery of the balloon structure to follow an extended path along the body space wall. The interior end section of the tubular structure of the catheter assembly deferring the drain passage is maintained in a generally central interior position which is unaffected by the inflation of the balloon structure in so far as its position is concerned. However, the drain openings contained therein are shielded from being obstructed by tissue defining the body space by virtue of the configuration of the balloon structure when inflated, the configuration being such that the tissue unobstructive function is achieved while at the same time providing an open final extent into the drain openings within the enhanced fluid circulating path provided.

Because the catheter assembly of the present invention extends through a surgical opening leading to the body cavity being treated, it is preferable to exteriorly cover the surgical opening and the cannulated catheter assembly with a collection bag. Such bags are known and usually consist essentially of a flexible bag having a skin engaging apertured adhesive pad fixed around an inlet aperture thereof and arranged to adhere to the portion of the patient's skin surrounding the surgical opening in a position such that any drainage from the surgical opening will pass into the collection bag through the pad aperture and the aligned bag inlet aperture. The bag also includes a spaced outlet through which the catheter assembly extends. An improvement in the bag structure in accordance with the principles of the present invention is to provide a patch of thickened resilient material on the periphery of the bag enabling the contents of the bag to be periodically removed without disturbing the connections or disrupting the sterility thereof as by the insertion of a needled syringe through the patch. The resilient material of the patch receives the syringe needle therethrough and is self-sealing in response to the withdrawal of the needle.

Accordingly, it is a further object of the present invention to provide a drainage bag structure for use with and in combination with a catheter assembly of the type described which is capable of accomplishing the improved functions noted above.

Another object of the present invention is to provide a catheter assembly of the type described which is simple in construction, effective in operation and economical to manufacture.

These and other objects of the present invention will become more apparent during the course of the following detailed description and appended claims.

The invention may best be understood with reference to the accompanying drawings, wherein an illustrative embodiment is shown.

In the drawings:

FIG. 1 is a somewhat schematic side elevational view illustrating two embodiments of catheter assemblies, constructed in accordance with the principles of the present invention, mounted in operative relation with a patient, each catheter assembly being shown in dotted lines in a second operative position;

FIG. 2 is a top plan view of the extremity of the interior end section of the catheter assembly of one of the embodiments with the balloon structure thereof in a deflated inserting condition;

FIG. 3 is a top plan view of the entire catheter assembly shown in FIG. 2 with the balloon structure shown in an inflated inserted condition;

FIG. 4 is an enlarged sectional view taken along the line of 4—4 of FIG. 3;

FIG. 5 is an enlarged sectional view taken along the line of 5—5 of FIG. 3;

FIG. 6 is an enlarged sectional view taken along the line of 6—6 of FIG. 3;

FIG. 7 is an enlarged sectional view taken along the line 7—7 of FIG. 3;

FIG. 8 is an enlarged sectional view taken along the line of 8—8 of FIG. 3;

FIG. 9 is an enlarged fragmentary sectional view taken along the line of 9—9 of FIG. 1;

Figures 10, 11, 12, 13:
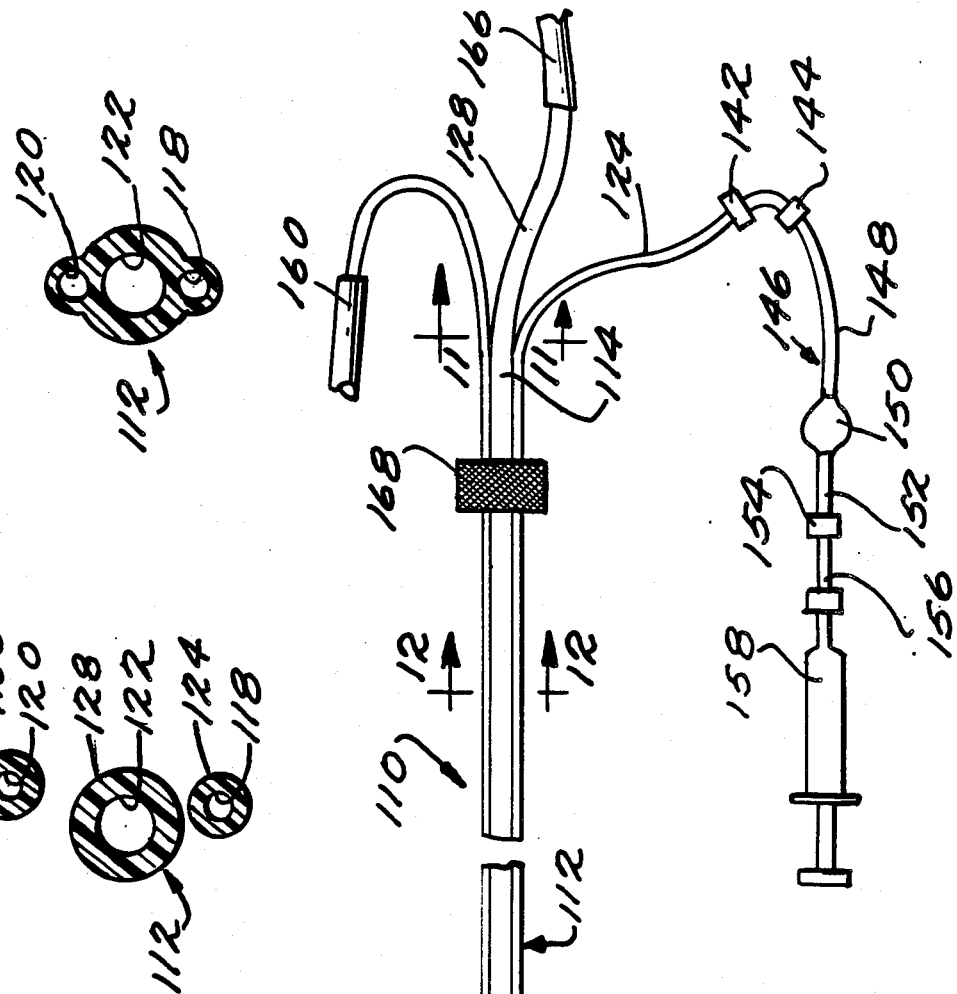
FIG. 10 is a view similar to FIG. 3, showing another embodiment of a catheter assembly embodying the principles of the present invention.
FIG. 11 is an enlarged sectional view taken along the line of 11—11 of FIG. 10.
FIG. 12 is an enlarged sectional view taken along the line of 12—12 of FIG. 10.
FIG. 13 is an enlarged sectional view taken along the line of 13—13 of FIG. 10.

Referring now more particularly to the drawings, there is shown in FIGS. 2 through 8 thereof one form of catheter assembly, generally indicated at 10, which embodies the principles of the present invention. As best shown in FIG. 3, the catheter assembly 10 includes an elongated flexible tubular structure, generally indicated at 12, having an exterior end section 14 and an adjacent opposite interior end section 16. The tubular structure 12 includes three separate fluid passages 18, 20 and 22, which extend within and between the exterior and interior end sections 14 and 16. The interior end section 16 is adapted in operation to be disposed within the patient, while the exterior end section 14 is adapted in operation to be disposed exteriorly of the patient. The tubular structure 12 is formed of a suitable flexible material, as, for example, an elastomeric resinous material, preferably, Silicone or a Silastic derivative.

As best shown in FIG. 4, the outer portion of the exterior end section 14 of the tubular structure 12 is formed of three separate tubes 24, 26 and 28 which define therein the exterior portions of the passages 18, 20 and 22 respectively. As best shown in FIG. 5, at the inner portion of the exterior end section 14, the three separate tubes become merged together into a single unitary construction in which the passage 22 is disposed centrally between the passages 18 and 20 in parallel relation therewith. The inner portion of the exterior end section 14 is also of similar unitary construction. At the outer portion of the interior end section 16, the portion of the unitary construction of the tubular structure 12 defining the adjacent end of the passage 18 is bifurcated, as indicated at 30, so as to communicate the passage 18 with the interior of a balloon structure in the form of a pair of inflatable balloon elements 32. It will be understood that the balloon structure may include three or more than three balloon elements rather than two as shown. Each balloon element 32 in its deflated condition, as shown in FIG. 2, is of elongated tapered end configuration, being fixed longitudinally along an inward wall portion 34 to the adjacent side of a central tube section or portion 36 of the tubular structure 12 defining the outer interior end portion of the central passage 22.

Passage 20 at a position adjacent the inner tapered ends of the balloon elements 32 leads into a pair of diverging tube portions 38 which define the outer interior ends of the passage 20 of the tubular structure 12. Each of the two tube portions 38 is fixed longitudinally along an outward wall portion 40 of the associated balloon element 32 opposite from the inward wall portion 34 thereof, fixed to the central tube portion 36.

Passage 18 serves as a communication medium through which balloon elements 32 can be inflated after the interior end section 16 of the tubular structure 12 has been inserted through the surgical opening into the body space to be treated. To facilitate the inflation of the balloon elements 32, the outer extremity of tube portion 24 is provided with a valved fitting 42 to cooperatively receive a second valved fitting 44 formed on the end of an inflation-deflation assembly 46. The valves of fittings 42 and 44 are open in response to the interconnection of the fittings and are closed in response to the disconnection of the fittings in accordance with standard practice.

Assembly 46 includes a tube 48 which carries the valved fitting 44 on one end thereof. The opposite end of the tube 48 is connected with a palpable manometric bulb 50 which accommodates pressure pulsations in the assembly 46. A short section of tubing 52 connects the bulb 50 to a pressure relief valve 54 which protects against over inflation of the balloon elements 32. A fitting 56 is connected to the opposite side of the pressure relief valve 54 to receive a syringe 58 which serves as the pump of the assembly 46 for inflating and deflating the balloon elements 32. In accordance with conventional practice the inflation-deflation medium may either be air or sterile water.

The positions of tube portions 36 and 38 with respect to the balloon elements and the configuration of the balloon elements 32 insures that treatment fluid introduced into passage 20 through a supply tube 60 suitably connected with the extremity of tube portion 26 will pass into the body space of the patient through a series of inlet openings 62 formed within the tube portions 38 in longitudinally spaced relation in such a way as to follow an extensive flow path therein. In this regard it will be noted that when the balloon elements 32 are in a deflated condition suitable for insertion or withdrawal, such as shown in FIG. 2, the inlet openings 60 within the tube portions 38 are closely adjacent a series of drain openings 64 formed in longitudinally spaced relation in opposite sides of the central tube section 36. The inflation of the balloon elements 32 extends the inward wall portions 34 and expands the outward wall portions 40 between the inlet openings 62 and drain openings 64 so as to greatly extend the path of flow from the inlet openings to the outlet openings. This more extensive flow path is initially established along the wall of the body space as the fluid passes from the inlet openings and is finally established along the spaces between the extended inward wall portions 34, which lead into the drain openings 64 in the central tube section 36. In this way drain openings 64 are maintained substantially operationally free of obstruction by tissue defining the body space of the patient. The fluid and other flowable material entering drain openings 64 in tube section 36 flow through passage 22 and are discharged into a drain tube 66 leading to a collection reservoir (not shown). The extensive flow path established along the wall of the body space being treated is particularly desirable in treating abscesses within the body space since a flow along the wall where the abscess material needs to be removed is established. Moreover, removal of the dislodged material from the body space is practically insured since the drain openings 64 are practically prevented from blockage by body tissue defining the body space being treated.

Where the catheter assembly 10 is used for peritoneal dialysis or other treatment necessitating a sterile interior condition, a contamination barrier in the form of a Dacron sleeve 68 is fixed around the inner portion of the interior end section 16 of the tubular structure 12 so as to be disposed within the body space during operation. If desired, more than one such sleeve 68 may be utilized.

FIG. 1 illustrates somewhat schematically the catheter assembly 10 in its operative position during peritoneal dialysis (or pelvic abscess). The dotted line showing indicates the position of the interior end section 16 during treatment of perienteric abscess or pancreatitis. It will be noted that there is provided at the juncture between the interior end section 16 and the exterior end section 14 of the tubular structure 12, a collection bag assembly 70 which serves to exteriorly collect any drainage that may seep from the surgical opening through which the catheter assembly 10 is inserted and withdrawn from the body space to be treated.

As shown in FIG. 1, the collection bag assembly 70 includes a bag 72 of thin flexible material, such as a thermoplastic resin, preferably polyvinyl chloride. The bag includes an inlet opening 74 and a spaced opening 76 through both of which the tubular structure 12 of the catheter assembly extends. The exterior surface of the bag 72 surrounding opening 74 is fixed as by an adhesive or the like to an apertured adhesive pad 78 which serves to fix the inlet opening of the bag to the patient's skin disposed in surrounding relation to the surgical opening. The spaced opening 76 which permits the tubular structure 12 of the catheter assembly 10 to pass out of the bag 72 is suitable sealed (e.g. by adhesive tape) to the exterior surface of the tubular structure after the latter has been positioned therethrough.

An important improvement in the collection bag assembly 70 in accordance with the principles of the present invention is illustrated in FIG. 9. As shown a portion of the wall of the bag 72 between openings 76 and 74 is provided with a patch 80 of thickened resilient material such as an elastomeric resin, preferably, elastomeric polyvinyl chloride. The patch material is operable to exteriorly sealingly receive a syringe needle (not shown) therethrough for purposes of emptying the contents of the bag without disturbing the bag connections or sterility. The material of the patch also is operable to self seal in response to the withdrawal of the syringe needle therefrom.

Referring now more particularly to FIGS. 10–13, there is shown therein another form of catheter assembly 110 embodying the principles of the present invention. The catheter assembly 110 is like the catheter assembly 10 already described except for certain differences in the balloon structure and related portions of the tubular structure. Since the remainder of the catheter assembly 110 is the same as the corresponding remainder of the catheter assembly, the corresponding elements of the catheter assembly 110 have been designated in the drawings with the same reference numerals preceded by the numeral 1 as those used in connection with the catheter assembly 10. Moreover, it is not believed essential that the description of these common elements be repeated.

The balloon structure of the catheter assembly 110 differs from that of the catheter assembly 10 in that it consists of only one elongated balloon element 132 which is communicated at one end with the passage 118, as indicated at 130. The balloon element 132 is shaped into a helical configuration and has its inward periphery fixed as indicated at 134 in helical relation along the periphery of a central tube section 136. The outward periphery of the helical balloon element 132 is fixed to a tube portion 138, as indicated at 140. Tube portion 138 has inlet openings 162 formed therein which correspond with the inlet openings 62 previously described, while tube section 136 includes drain openings 164 which correspond with the drain openings ;64 previously described.

FIG. 1 illustrates the catheter assembly 110 in an operative position suitable for performing peritoneal dialysis and for treating pericolonic abscess, perihepatic abscess, perinephric abscess, paragastro-duodenal abscess, retroperitoneal abscess and pancreatic abscess. The position shown in dotted lines is suitable for treating empyema or any body abscess accessible to the catheter lengths.

The manner in which the catheter 110 is used in treating the above as well as the various treatments attributable to the catheter assembly 10 in the positions thereof shown in FIG. 1, both in solid and in dotted lines, is believed to be apparent from the description set forth above. The catheter assemblies are both inserted with the balloon structure in deflated condition with the use of a conventional guide wire inserted in one or more of the passages. During operation the balloon elements are inflated which establishes the more extensive flow path for the treatment fluid passing into the body space through the inlet openings 62 or 162. The path established by the interrelation between the inlet openings and the balloon structure whether of the two element configurations of the catheter assembly 10 or the helical single element of the catheter assembly 110 is effective in contacting the walls of the body space with fluid so as to interact with the abscess condition therein or to allow more effective exchange during peritoneal dialysis. Effective drainage is provided in both catheter assemblies through centrally located drain openings which are maintained in a substantially unobstructed condition during operation.

In addition to the normal use of the catheter assemblies 10 and 110, it should be noted that the arrangement enables the same to be used in what may be referred to as a sump mode, a mode which may be found desirable in all of the treatments previously mentioned except for peritoneal dialysis. The sump mode is one that can be utilized after conventional irrigation into the abscessed body space has been accomplished through irrigation fluid communicated with supply tube 60 or 160. By unhooking the supply tube 60 or 160 the passage 20 or 120 within tube portion 26 or 126 becomes a source of air which may pass into the abscessed body space through openings 62 or 162. This air flow can be induced by hooking the drain tube 66 or 166 to an intermittent or constant air suction source (not shown). This circuit enables air to be used as a medium for transport of cavity drainage.

It thus will be seen that the objects of this invention have been fully and effectively accomplished. It will be realized, however, that the foregoing preferred specific embodiment has been shown and described for the purpose of illustrating the functional and structural principles of this invention and is subject to change without departure from such principles. Therefore, this invention includes all modifications encompassed within the spirit and scope of the following claims.

What is claimed is:

1. A catheter assembly for insertion through a surgical opening into an interior body space for enabling a fluid to be introduced into said body space and for enabling unwanted flowable material to be drained from said body space including fluid after the same has been introduced therein, said catheter assembly comprising an elongated flexible tubular structure having an exterior end section, an opposite interior end section operable to be inserted within a body space and three separate fluid passages extending within said exterior and interior end sections, a balloon structure carried by the interior end section of said tubular structure in communication with a first of said three separate passages, a second of said three separate passages having inlet opening means communicating therewith at the exterior end section of said tubular structure through which fluid is introduced and outlet opening means communicating therewith at the interior end section of said tubular structure through which fluid introduced through said inlet opening means is introduced into said body space, a third of said three separate passages having drain opening means communicating therewith at the interior end section of said tubular structure through which fluid and/or unwanted flowable material in the body space can pass and discharge opening means communicating therewith at the exterior end section of said tubular structure through which fluid and/or flowable material passing through said drain opening means is discharged, said first passage having inflation opening means communicating therewith at the exterior end section of said tubular structure through which inflating fluid is received for passage into said balloon structure to inflate the same after the interior end section of said tubular structure has been inserted into said body space so as to cause fluid passing into the body space through said outlet opening means to follow a more extensive flow path within said body space in order to reach said drain opening means and said drain opening means to be maintained substantially operationally free of obstruction by tissue defining said body space than is the case when said balloon structure is deflated within said body space immediately following insertion therein or just prior to withdrawal therefrom, said balloon structure being configured so that in the inflated condition thereof within said body space the inflated surfaces thereof include outer portions facing toward the walls defining the body space and inner portions defining flow paths directed inwardly from the walls defining the body space, the interior end section of the tubular structure defining the second passage communicating with said outlet opening means being carried by the outer surface portions of said balloon structure so that the fluid passing therethrough enters the body space adjacent the walls thereof and is confined to flow therealong until reaching an inwardly directed flow path defined by said balloon structure inner portions, the interior end section of said tubular structure defining the third passage leading from said drain opening means being disposed at the central interior of said balloon structure so that said drain opening means receives fluid after passing along the inwardly directed flow paths defined by the inner surface portions of said balloon structure.

2. A catheter assembly as defined in claim 1 wherein the interior end section of said tubular structure defining the third passage leading from said drain opening means includes a separate tube section, said drain opening means comprising a series of separate drain openings spaced longitudinally along said separate tube section.

3. A catheter assembly as defined in claim 2 wherein said balloon structure includes a plurality of balloon elements disposed in annularly spaced relation about said separate tube section in substantially longitudinally coextensive relation thereto.

4. A catheter assembly as defined in claim 3 wherein said plurality of balloon elements are fixed at annularly spaced portions longitudinally along the length of said separate tube section.

5. A catheter assembly as defined in claim 4 wherein the drain openings spaced longitudinally along said separate tube section are formed in the periphery of the separate tube section at positions between adjacent positions of balloon element fixture therewith.

6. A catheter assembly as defined in claim 2 wherein said balloon structure includes an elongated balloon element disposed in helically surrounding relation to said separate tube section.

7. A catheter assembly as defined in claim 6 wherein said elongated balloon element includes opposite ends and an intermediate portion between said opposite ends, said opposite ends being fixed in spaced relation to said separate tube section, said intermediate portion being disposed in helically surrounding relation with said separate tube section and being free from fixed connection therewith.

* * * * *